United States Patent
Chamberland et al.

(10) Patent No.: US 7,410,974 B2
(45) Date of Patent: Aug. 12, 2008

(54) HALOGENATED QUINAZOLINYL NITROFURANS AS ANTIBACTERIAL AGENTS

(75) Inventors: Suzanne Chamberland, Eastman (CA); Francois Malouin, Eastman (CA)

(73) Assignee: Ulysses Pharmaceutical Products, Inc., Eastman, Quebec (CA)

(*) Notice: Subject to any disclaimer, the term of this patent is extended or adjusted under 35 U.S.C. 154(b) by 5 days.

(21) Appl. No.: 10/567,660

(22) PCT Filed: Aug. 6, 2004

(86) PCT No.: PCT/CA2004/001466

§ 371 (c)(1),
(2), (4) Date: Feb. 8, 2006

(87) PCT Pub. No.: WO2005/014585

PCT Pub. Date: Feb. 17, 2005

(65) Prior Publication Data

US 2006/0258693 A1     Nov. 16, 2006

Related U.S. Application Data

(60) Provisional application No. 60/493,336, filed on Aug. 8, 2003.

(51) Int. Cl.
*A61K 31/517* (2006.01)
*C07D 239/94* (2006.01)

(52) U.S. Cl. .................. 514/266.2; 544/293

(58) Field of Classification Search ............ 514/235.8, 514/237.2, 266.2; 544/116, 284, 293
See application file for complete search history.

(56) References Cited

U.S. PATENT DOCUMENTS

| | | | |
|---|---|---|---|
| 3,324,122 A | 6/1967 | Burch | |
| 3,542,784 A | 11/1970 | Burch | |
| 3,970,648 A | 7/1976 | Horn et al. | |
| 3,973,021 A | 8/1976 | Horn et al. | |
| 3,974,277 A | 8/1976 | Horn et al. | |
| 5,436,233 A | 7/1995 | Lee et al. | |
| 5,439,895 A | 8/1995 | Lee et al. | |
| 6,184,377 B1 | 2/2001 | Gao | |
| 6,306,864 B1 | 10/2001 | Welch, Jr. | |
| 6,380,204 B1 | 4/2002 | Chenard et al. | |
| 6,429,311 B2 | 8/2002 | Gao | |
| 6,479,499 B1 | 11/2002 | Kuo et al. | |
| 2001/0018518 A1 | 8/2001 | Gao | |
| 2002/0025968 A1 | 2/2002 | Pamcku et al. | |
| 2002/0161014 A1 | 10/2002 | Chanchal et al. | |
| 2003/0125344 A1 | 7/2003 | Nagarathnam | |
| 2003/0220357 A1 | 11/2003 | Bankston et al. | |
| 2004/0043987 A1 | 3/2004 | Gouliaev et al. | |
| 2004/0131628 A1 | 7/2004 | Bratzler et al. | |

FOREIGN PATENT DOCUMENTS

| | | |
|---|---|---|
| BE | 672504 | 3/1966 |
| DE | 2140280 | 2/1972 |
| GB | 1168430 | 10/1969 |
| WO | WO 98/34111 A1 | 8/1998 |
| WO | WO 98/34115 A1 | 8/1998 |
| WO | WO 01/81346 A3 | 11/2001 |
| WO | WO 03/091224 A1 | 11/2003 |
| WO | WO 2004/004658 A2 | 1/2004 |
| WO | WO 2005/014585 A1 | 2/2005 |

OTHER PUBLICATIONS

Burch, Homer A., "Nitrofuryl heterocycles, IV.4-Amino-2-(5-nitro-2-furyl) quinazoline derivatives" *Journal of Medicinal Chemistry* (1966), 9(3), 408-10.

Cohen, Samuel M. et al., "Comparative carcinogenicity of 5-nitrothiophenes and 5-nitrofurans in rats" *Journal of the National Cancer Institute* (1976), 57(2), 277-82.

Desos, Patrice et al., "Structure-Activity Relationships in a Series of 2[1H]-Quinolones Bearing Different Acidic Function in the 3-Position: 6,7 Dichloro-2[1H]-oxoquinoline-3-phosphonic Acid, a New Potent and Selective AMPA/Kainate Antagonist with Neuroprotective Properties" *Journal of Medicinal Chemistry* (1966) 39(1) 197-206.

(Continued)

*Primary Examiner*—James O. Wilson
*Assistant Examiner*—Tamthom N Truong
(74) *Attorney, Agent, or Firm*—Klarquist Sparkman LLP (57) ABSTRACT

The present invention includes novel compounds of the formula (I) wherein X is absent or trans or cis CHCH, $R_1$ is $(C_1\text{-}C_{10})$ alkyl unsubstituted or substituted by one to three hydroxy, $(C_1\text{-}C_{10})$ alkenyl unsubstituted or substituted by one to three hydroxy, $(C_1\text{-}C_{10})$ alkynyl unsubstituted or substituted by one to three hydroxy, or aryl unsubstituted or substituted by one to three hydroxy; $R_2$ is hydrogen, alkyl or aryl; $R_3$ and $R_4$ are, independently of each other, H, halogen, or a solubilizing group, with the provisio that at least one of $R_3$ and $R_4$ is halogen; and pharmaceutically acceptable salts thereof. The invention also includes pharmaceutically acceptable formulations of said compounds which exhibit antibiotic activity against a wide spectrum of microorganisms including organisms which are resistant to multiple antibiotic families and are useful as antibacterial agents for treatment or prophylaxis of bacterial infections, or their use as antiseptics, agents for sterilization or disinfection.

9 Claims, 3 Drawing Sheets

OTHER PUBLICATIONS

Gupta, K. "Addressing Antibiotic Resistance" *Dis. Mon.* (2003) 49(2) 99-110.

Hour, Mann-Jen "6-Alkylamino- and 2,3 Dihydro-3'-methoxy-2-phenyl-4-quinazolinones and Related Compunds: Their Synthesis, Cytotoxicity, and Inhibition of Tubulin Polymerization" *Journal of Medicinal Chemistry* (2000) 43(23) 4479-4487.

Jiang, Jack B. et al. "Synthesis and biological evaluation of 2-styrylquinazolin-4(3H)-ones, a new class of antimitotic anticancer agents which inhibit tubulin polymerization" *Journal of Medicinal Chemistry* (1990) 33(6) 1721-28.

Molina, Enrique et al., "Designing Antibacterial Compounds through a Topological Substructural Approach" *Journal of Chemical Information and Computer Sciences* (2004), 44(2), 515-521.

Moskalenko, N. Yu et al., "4-Amino-2-styrylquinazolines,— a new class of antiprotozoal drugs" *Khimiko-Farmatsevticheskii Zhurnal* (1986), 20(4), 437-46.

Nicolle, L.E. "Urinary Tract Infection: Traditional Pharmacologic Therapies" (2003) 49(2) 111-128.

Ogawa, Nobuo et al. "Synthesis and histamine H2-antagonist activity of 4-quinzolinione derivatives" *Chemical & Pharmaceutical Bulletin* (1988) 36(8) 2955-67.

Van Natta, J.P. et al., "Determination of untreated whole-milk effects on in vitro antibacterial activity" *Applied Microbiology* (1970), 19(2), 220-23.

Yakhontov, L.N. et al., "Synthesis and Study of Biological Activity of Substituted 4-Amino-2-Styrylquinazolines" *Khimiko-Farmatsevticheskii Zhurnal* (1975)9(11) 12-18.

Zhikhareva, G.P. et al., "Synthesis and Anti-Inflammatory Activity of Substituted 2-styryl-4-ŏ-diethylamino-αmethylbutylamino)-6-nitro and 2-styryl-4-(ó-diethylamino-α-methylbutylamino)-6-aminoquinazolines" *Khimiko-Farmatsevtiheskii Zhurnal* (1980) 14(2), 45-49.

Zhikhareva, G.P. et al., "Synthesis and Antiviral Activity of Substituted 4-(ŏ-diethylamino-αmethylbutylamino)-2-styrylquinazolines" *Khimiko-Farmatsevtichesii Zhurnal*(1978) 12(11) 44-48.

Supplementary European Search Report for Application No. EP 04 76 1630, 2 pages, dated Nov. 11, 2006.

Moskalenko, N. Yu, et al., "4-Amino—styrylquinazolines—a new class of antiprotozoal drugs," *Database Caplus [Online] Chemical Abstracts Service*, XP002404560 retrieved from STN, Database accession no. 1987:32975, 2 pages.

Khimiko-Farmatsevtichesii Zhurnal, 20(4), 437-446, Coden: KHFZAN; ISSN: 0023-1134, 1986, XPoo2917813. (*See cite No. C8 on Information Disclosure Statement dated Jun. 20, 2006.*).

Aicher et al., "Secondary Amides of (*R*)-3,3,3-Trifluoro-2-hydroxy-2-methylpropionic Acid as Inhibitors of Pyruvate Dehydrogenase Kinase," *J. Med. Chem.* 43:236-249, 2000.

Almansa et al., "Synthesis and Structure—Activity Relationship of a New Series of COX-2 Selective Inhibitors: 1,5-Diarylimidazoles," *J. Med. Chem.* 46:3463-3475, 2003.

Pagani et al., "Synthesis and in Vitro Anti-*Mycobacterium* Activity of N-Alkyl-1,2-dihydro-2-thioxo-3-pyridinecarbothioamides. Preliminary Toxicity and Pharmacokinetic Evaluation," *J. Med. Chem.* 43:199-204, 2000.

Youngman et al., "α-Substituted *N*-(Sulfonamido)alkyl-β-aminotetralins: Potent and Selective Neuropeptide Y Y5 Receptor Antagonists," *J. Med. Chem.* 43:346-350, 2000.

Figure 1. Time-kill curve for Example I (Compound V), Example VII (Compound XV), and ciprofloxacin against *S. aureus* ATCC 29213.

Figure 2. Time-kill curve for Example I (Compound V) and ciprofloxacin against *E. coli* ATCC 25922.

Figure 3. In vivo activity of compound Example I in a *S. aureus* model of systemic infection in the mouse.

HALOGENATED QUINAZOLINYL NITROFURANS AS ANTIBACTERIAL AGENTS

CROSS-REFERENCE TO RELATED APPLICATIONS

This is a U.S. National Stage of International Application No. PCT/CA2004/001466, filed Aug. 6, 2004, which claims the benefit of U.S. Provisional Application No. 60/493,336 filed Aug. 8, 2003, both of which are incorporated herein by reference.

FIELD OF THE INVENTION

This invention relates to novel nitrofuran antibiotics and their use for the treatment or prophylaxis of bacterial infections in humans or animals, or their use as antiseptics, sterilizants or disinfectants. These compounds exhibit antibiotic activity against a wide spectrum of microorganisms, including organisms which are resistant to multiple antibiotic families.

BACKGROUND OF THE INVENTION

The following review of the background of the invention is merely provided to aid in the understanding of the present invention and neither it nor any of the references cited within it are admitted to be prior art to the present invention.

Management of nosocomial or community-acquired bacterial infections is becoming very difficult due to the emergence of bacteria resistant to one or multiple families of antibiotics. Unfortunately, the widespread and indiscriminant use of antibiotics has led to a rapid increase in the number of bacterial strains which are resistant to antibiotics. Most importantly, resistance has emerged among clinically important microorganisms which threaten the utility of the currently available arsenal of antibiotics. A global trend of increasing resistance to antibiotics, with wide variations according to geographical areas, is well documented by the World Health Organization and in the scientific literature.

There is a need for novel and effective antibiotics that are particularly active against microorganisms which are resistant to currently available drugs. For example, resistance of bacteria causing urinary tract infections to trimethoprim-sulfamethoxazole, β-lactams and fluoroquinolones is becoming a major factor in the management of such infections. Despite the use of nitrofuran antibiotics for several decades, mainly for the treatment of urinary tract infections, resistance to agents of this family has remained low (0-2%) in microorganisms most commonly encountered (Gupta K. Addressing antibiotic resistance. Dis Mon. 2003 February; 49(2):99-110; Nicolle LE. Urinary Tract Infection: Traditional pharmacologic therapies. 2003. February; 49(2):111-128).

U.S. Pat. Nos. 3,970,648, 3,973,021 and 3,974,277 disclose nitrofurans of the following formulae: 2-[2-(5-nitro-2-furyl)vinyl]-4-(anilino)quinazoline, 2-[2-(5-nitro-2-furyl)vinyl]-4-(p-hydroxyanilino)-quinazoline, 2-[2-(5-nitro-2-furyl)vinyl]-4-(o-hydroxyanilino)-quinazoline, and 2-[2-(5-nitro-2-furyl)vinyl]-4-(m-hydroxyanilino)-quinazoline. These patents teach the use of these compounds as pesticides and animal growth promotants for improving feed efficiency in animals such as poultry, swine and cattle. Although these molecules gained the property of being adequate edible feed additives for animal growth promotion compared to quinazoline molecules having the nitrofuran group directly attached to it (U.S. Pat. No. 3,542,784), a drawback of the compounds from the above patents (U.S. Pat. Nos. 3,970,648, 3,973,021 and 3,974,277) is that the patents teach that they are now devoid of activity against important pathogens such as *Escherichia coli*, *Staphylococcus aureus* and *Salmonella*. It would be desirable to obtain nitrofurans which provide significant improvement of potency and expand the antimicrobial spectrum of activity. This means that lower amounts of compounds are required for in vitro and in vivo (in animals) antimicrobial action against a wider variety of pathogens affecting animals and humans.

Besides, there are only a few nitrofuran antibiotics currently used in humans for the treatment of infectious diseases and one is known by the generic name nitrofurantoin (commercial names include: Macrobid, Macrodantin, Furadantin). It is used in adults and children to treat acute urinary tract infections and to prevent recurrent urinary tract infections. A drawback of nitrofurantoin is that it does not have good potency (i.e., relatively high amounts are required to exert its antibacterial activity) and it does not have a wide spectrum of antimicrobial activity, which limits the use of this compound in treating bacterial infections.

Novel nitrofurans with superior antimicrobial potency and improved pharmacological properties, would provide an alternative for the treatment of severe infections caused by antibiotic-susceptible and -resistant microorganisms.

SUMMARY OF THE INVENTION

The compounds described herein can be used as antibiotics for the treatment or prophylaxis of bacterial infections, or as antiseptics, sterilizants, or disinfectants.

The general structural feature of the compounds is a nitrofuran linked to the 2 position of a quinazoline directly or via a vinyl group. It is believed that the nitrofuran is essential for antimicrobial activity while the quinazoline in particular as substituted, e.g., with an halogen and/or a methylpiperazino group, improves potency, expands the spectrum of activity (e.g., activity against *E. coli*, *S. aureus*, *Salmonella*, *Mycobacterium*, anaerobic bacteria and microorganisms that are resistant to multiple antibiotics), provides a bactericidal (lethal) activity (i.e., as opposed to a bacteriostatic growth-inhibitory activity), provides in vivo activity, and improves solubility.

The quinazoline contains one or two functional groups at the 4 position attached via an amine, and a hydrogen, halogen, or solubilizing group (such as an amine containing heterocyclic group, or more preferably an amine containing heterocyclic group which further contains at least one oxygen or nitrogen group) at the 6 or 7 position with the proviso that at least one of the 6 or 7 positions are substituted with a halogen.

This invention includes compounds of the following general formula:

(1.0)

wherein
X is absent or trans or cis CHCH,
$R_1$ is $(C_1-C_{10})$alkyl unsubstituted or substituted by one to three hydroxy, $(C_1-C_{10})$alkenyl unsubstituted or substituted by one to three hydroxy, $(C_1-C_{10})$alkynyl unsubstituted or substituted by one to three hydroxy, or aryl unsubstituted or substituted by one to three hydroxy;

$R_2$ is hydrogen, alkyl or aryl;

$R_3$ and $R_4$ are, independently of each other, H, halogen, or a solubilizing group, with the proviso that at least one of $R_3$ and $R_4$ is halogen;

and pharmaceutically acceptable salts thereof.

Preferably the solubilizing group is (1.2)

wherein:

P and R are each independently selected from $CH_2$, $CH_2CH_2$ and $CH_2CHT$ where T is alkyl, and Q is O, S, NH or $NCH_3$.

The invention also includes pharmaceutically acceptable formulations of said compounds which exhibit antibiotic activity against a wide spectrum of microorganisms including organisms which are resistant to multiple antibiotic families and are useful as antibacterial agents for treatment or prophylaxis of bacterial infections, or their use as antiseptics, agents for sterilization or disinfection. In another aspect of the present invention there is provided compositions comprising the compounds of the invention. In yet another aspect of the present invention there is provided processes for preparing the compounds of the invention. Certain terms that are used in this application are defined below.

The term "alkyl" refers to the radical of saturated aliphatic groups including straight chain alkyl groups, branched-chain alkyl groups, cycloalkyl (alicyclic) groups, alkyl substituted cycloalkyl groups, and cycloalkyl substituted alkyl groups. Typical alkyl groups include, but are not limited to, methyl, ethyl, propyl, isopropyl, butyl, isobutyl, t-butyl, pentyl, isopentyl, hexyl, etc. The alkyl groups is preferably $(C_1-C_{10})$ alkyl, and more preferably $(C_1-C_6)$alkyl and even more preferably $(C_2-C_4)$ alkyl.

The term "alkyl" can encompass heteroalkyl groups wherein one or more carbons of the hydrocarbon backbone are replaced with a heteroatom, e.g. N, O or S. The term "alkyl" can encompass a "substituted alkyl" having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), $-CF_3$, $-CN$ and the like. Exemplary substituted alkyls are described below. Cycloalkyls can be further substituted with alkyls, alkenyls, alkoxys, alkylthios, aminoalkyls, carbonyl-substituted alkyls, $-CF_3$, $-CN$, and the like. Any substituted alkyl may have 1 to 5 substituents or any combinations of 1 to 5 substituents.

The terms "alkenyl" and "alkynyl" refer to unsaturated aliphatic groups analogous in length and possible substitution to the alkyls described above, preferably $(C_2-C_{10})$, and more preferably $(C_2-C_6)$ alkyl and even more preferably $(C_2-C_4)$, but that contain at least one double or triple bond respectively. An "alkenyl" is an unsaturated branched, straight chain, or cyclic hydrocarbon radical with at least one carbon-carbon double bond. The radical can be in either the cis or trans conformation about the double bond(s). Typical alkenyl groups include, but are not limited to, ethenyl, propenyl, isopropenyl, butenyl, isobutenyl, tert-butenyl, pentenyl, hexenyl, etc. An "alkynyl" is an unsaturated branched, straight chain, or cyclic hydrocarbon radical with at least one carbon-carbon triple bond. Typical alkynyl groups include, but are not limited to, ethynyl, propynyl, butynyl, isobutynyl, pentynyl, hexynyl, etc.

The term "aryl" refers to aromatic radicals having 3-14 ring atoms and at least one ring having a conjugated pi electron system. Preferably at least two, more preferably at least four, of the ring atoms are carbon atoms. For example aryl may be a $C_5, C_6, C_7, C_8, C_9$ or $C_{10}$ ring. The term "aryl" encompasses "heteroaryl" compounds. The term "heteroaryl" refers to an aromatic heterocyclic group usually with one or more heteroatoms selected from O, S and N in the ring. Examples of aryl include without limitation phenyl, substituted phenyl, pyridyl, substituted pyridyl, pyridinyl, substituted pyridinyl, thiophenyl, substituted thiophenyl, furanyl, substituted furanyl, thiazole, oxazole or substituted or unsubstituted imidazole. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted aryl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), $-CF_3$, $-CN$ and the like. Such substituted aryl may have 1 to 5 substituents or any combinations of 1 to 5 substituents.

The term "halogen" refers to fluoro, chloro, bromo or iodo or fluoride, chloride, bromide or iodide or fluorine, chlorine, bromine or iodine.

The present invention includes the pharmaceutically acceptable salts of the compounds defined by general formula 1.0.

The term "pharmaceutically acceptable salt" as used herein, refers to salts of the compounds of the invention which are substantially nontoxic to living organisms e.g. sulfate, pyrosulfate, bisulfate, sulfite, bisulfite, phosphate, monohydrogenphosphate, dihydrogenphosphate, metaphosphate, pyrophosphate, bromide, hydrobromide, iodide, acetate, propionate, decanoate, caprate, caprylate, acrylate, ascorbate, formate, hydrochloride, dihydrochloride, isobutyrate, caproate, heptanoate, propiolate, glucuronate, glutamate, propionate, phenylpropionate, salicylate, oxalate, malonate, succinate, suberate, sebacate, fumarate, malate, maleate, hydroxymateate, mandelate, mesylate, nicotinate, isonicotinate, cinnamate, hippurate, nitrate, stearate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydrozybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, alpha-hydroxybutyrate, glycolate, tartrate, hemitartrate, benzenesulfonate, methanesulfonate, ethanesulfonate, propanesulfonate, hydroxyethanesulfonate, 1-naphthalenesulfonate, 2-naphthalenesulfonate, 1,5-naphthalenedisulfonate, mandelate, tartarate and the like.

DETAILED DESCRIPTION

Compounds of the present invention generally contain a nitrofuran linked to a quinazoline ring directly or by a vinyl group. The quinazoline ring contains one or two functional groups at the 4 position attached via an amine, a halogen at the 6 position or 7 position or both and at either the 6 position or 7 position, a hydrogen, a halogen or solubilizing group (such as an amine containing heterocycle or more preferably a heterocyclic containing at least one nitrogen and an oxygen or nitrogen group), and a nitrofuran moiety attached to the 2 position.

Compounds of the present invention can generally be made using the following methods. To 5-fluoro-anthranilamide hydrochloride is added, in steps, hydrochloric acid, acetic anhydride and aqueous ammonia, forming 6-fluoro-2-methyl-4-(3H)quinazolinone. Next 5-nitro-2-furancarboxaldehyde is added with acetic anhydride and sulfuric acid to form 6-fluoro-2-[2-(5-nitro-2-furyl)vinyl]-4-(3H)quinazolinone (III), which is used to prepare chloro and anilino derivatives. For example, phosphorus pentachloride and phosphorus oxychloride were added to form 6-fluoro-2-[2-(5-nitro-2-furyl) vinyl]-4-chloroquinazoline (IV) to which various functional groups can be added to the 4 position on the quinazoline. We refer to the Examples for a more detailed description of these methods.

Antimicrobial Data

Overview. In vitro and in vivo (in animals) tests have revealed the unique antimicrobial properties of 6-fluoro-2-[2-(5-nitro-2-furyl)vinyl]-4-(p-hydroxyanilino)-quinazoline and derivatives, and demonstrated that the spectrum of activity of these molecules is highly suitable for treatment of difficult-to-treat human infections. In particular, 6-fluoro-2-[2-(5-nitro-2-furyl)vinyl]-4-(p-hydroxyanilino)quinazoline and 7-(4-methylpiperazino)-6-fluoro-2-[2-(5-nitro-2-furyl) vinyl]-4-(p-hydroxyanilino)-quinazoline are highly potent broad-spectrum antibacterial agents that demonstrated activity against multiple Gram positive, Gram negative, acid-fast and anaerobic bacteria. Such a property is comparable, or better, to extremely potent commercial drugs of the macrolide, β-lactam, or fluoroquinolone class. Moreover, the nitrofurans of the present invention like 6-fluoro-2-[2-(5-nitro-2-furyl)vinyl]-4-(p-hydroxyanilino)-quinazoline and 7-(4-methylpiperazino)-6-fluoro-2-[2-(5-nitro-2-furyl)vinyl]-4-(p-hydroxyanilino)-quinazoline, being of a different structural class, are not affected by commonly found microbial mechanisms of resistance that have been developed over the recent years against most antimicrobial agents currently used clinically. Also, we were able to demonstrate that 6-fluoro-2-[2-(5-nitro-2-furyl)vinyl]-4-(p-hydroxyanilino) quinazoline, administrated by gavages, is active in vivo in a mouse model of infection, thus indicating oral bioavailability and relatively low toxicity. All these antimicrobial and chemical properties, represent those of a potent and safe antibiotic molecule.

In various embodiments, the nitrofurans of the present invention may be used therapeutically in formulations or medicaments to prevent or treat bacterial infections. The invention provides corresponding methods of medical treatment, in which a therapeutic dose of a nitrofuran of the present invention is administered in a pharmacologically acceptable formulation, e.g. to a patient or subject in need thereof. Accordingly, the invention also provides therapeutic compositions comprising a nitrofuran of the present invention, and a pharmacologically acceptable diluent, adjuvant, excipient or carrier. In one embodiment, such compositions include a nitrofuran of the present invention in a therapeutically or prophylactically effective amount sufficient to treat or prevent a bacterial infection. The therapeutic composition may be soluble in an aqueous solution at a physiologically acceptable pH.

A "therapeutically effective amount" refers to an amount effective, at dosages and for periods of time necessary, to achieve the desired therapeutic result, such as a reduction of bacterial infection. A therapeutically effective amount of a nitrofuran of the present invention may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the rate of bacterial infection-related disease onset or progression. A prophylactically effective amount can be determined as described above for the therapeutically effective amount. For any particular subject, specific dosage regimens may be adjusted over time according to the individual need and the professional judgment of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a nitrofuran of the present invention can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. a nitrofuran of the present invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a nitrofuran of the present invention may be formulated with one or more additional compounds that enhance the solubility of the nitrofuran.

In accordance with another aspect of the invention, therapeutic compositions of the present invention, comprising a nitrofuran of the present invention, may be provided in containers or commercial packages which further comprise instructions for use of the nitrofuran for the prevention and/or treatment of bacterial infection.

Accordingly, the invention further provides a commercial package comprising a nitrofuran of the present invention, or the above-mentioned therapeutic composition, together with instructions for the prevention and/or treatment of bacterial infection.

The invention further provides a use of a nitrofuran of the present invention for prevention and/or treatment of bacterial infection. The invention further provides a use of a nitrofuran of the present invention for the preparation of a medicament for prevention and/or treatment of bacterial infection.

The invention further provides a use of a nitrofuran of the present invention as an antiseptic, sterilizant, or disinfectant.

Now in order to more particularly define some embodiments of the present invention, the following Examples provide details of specific compounds of the invention, methods of producing the same and results from testing such compounds, particularly when X is trans or cis CHCH.

EXAMPLE I

6-Fluoro-2-methyl-4-(3H)quinazolinone (I)

5-Fluoro-anthranilamide hydrochloride was prepared by adding 20 ml of concentrated hydrochloric acid (37% by weight) to a solution of 27.3 g of 5-fluoro-anthranilamide in 200 ml of methanol. This mixture was cooled in an ice bath to precipitate the hydrochloride which was then collected and dried to obtain a product. A 17.4 g (0.1 mole) portion of the hydrochloride thus obtained was refluxed for 3 hours with 100 ml acetic anhydride and allowed to stand overnight. The mixture was then cooled in an ice bath and the solids collected by filtration on a Buchner funnel. The filter cake was slurried in 100 ml of water, and warmed to enhance dissolution and then 28% aqueous ammonia was added until the mixture was alkaline. After cooling, the 6-fluoro-2-methyl-4-(3H) quinazolinone precipitated as a solid, was then collected, washed with a small amount of cold water and dried at 70° C. to obtain the desired product.

5-nitro-2-furancarboxaldehyde (II)

A total of 86.5 g of 5-nitrofurfurylidine diacetate was added in small portions to 90 ml of sulfuric acid (73% by weight) over a period of 10 to 15 min. The mixture was stirred for 30 min at ambient temperature, 10 min at 50° C., cooled to 30° C., and then poured onto 150 g of crushed ice. The mixture was filtered, sucked as dry as possible on a Buchner funnel with the aid of a rubber dental dam and this afforded 51.5 g of 5-nitro-2-furancarboxaldehyde which melted at 32°-34° C.

6-fluoro-2-[2-(5-nitro-2-furyl)vinyl]-4-(3H) quinazolinone (III)

To 16 g (0.1 mole) 6-fluoro-2-methyl-4-(3H)quinazolinone were added 100 ml acetic anhydride, 0.5 ml 96% sulfuric acid and 20 g (0.14 mole) 5-nitro-2-furancarboxaldehyde and the mixture was stirred 2 hours at 50°-60° C. The reaction mixture was poured into water and boiled 10 min. After it stood overnight, the product was collected by filtration, washed with water, then methanol. A yellow solid was obtained. This solid 6-fluoro-2-[2-(5-nitro-2-furyl)vinyl]-4-(3H)quinazolinone was used to prepare the chloro-(IV) and anilino (V) derivatives described below.

6-fluoro-2-[2-(5-nitro-2-furyl)vinyl]-4-chloro-quinazoline (IV)

A 500 ml 3 necked flask fitted with a stirrer, reflux condenser and protected by a calcium chloride trap was charged with 9.0 g of phosphorus pentachloride (0.043 mole) and 70 ml of phosphorus oxychloride and the mixture stirred. To this 11.3 g (0.04 mole) of 6-fluoro-2-[2-(5-nitro-2-furyl)vinyl]-4-(3H)quinazolinone was added and rinsed into the flask with 15 ml of phosphorus oxychloride. The mixture was heated under reflux for 4 hours, cooled in an ice bath and diluted with 150 ml of diethyl ether. The 6-fluoro-2-[2-(5-nitro-2-furyl)vinyl]-4-chloroquinazoline which precipitated was collected by filtration, washed with 100-150 ml of diethyl ether, slurried in 100 ml of diethyl ether and then refiltered to obtain 8.09 g of the desired product.

6-fluoro-2-[2-(5-nitro-2-furyl)vinyl]-4-(p-hydroxyanilino)-quinazoline(V)

A 250 ml Erlenmeyer flask equipped with a magnetic stirrer and oil bath for heating was charged with 8.0 g (0.07 mole) of p-aminophenol and 25 ml of dimethylformamide. After the p-aminophenol was dissolved by stirring, (0.03 mole) of 6-fluoro-2-[2-(5-nitro-2-furyl)vinyl]-4-chloroquinazoline (IV) was added. The reaction mixture was then heated at 70° C.-90° C. for 2 hours after which 60 ml of water was added and the solution after cooling was placed in a refrigerator for crystallization. After 3 days, the brown yellow solid was collected, washed first with water, then methanol and then dried to obtain 7.20 g of product.

EXAMPLE II

6-fluoro-2-[2-(5-nitro-2-furyl)vinyl]-4-(m-hydroxyanilino)-quinazoline (VI)

An Erlenmeyer flask is charged with 4.8 g (0.044 mole) of m-aminophenol and 100 ml of dimethylformamide. The charge is stirred to dissolve the m-aminophenol and 6.5 g (0.02 mole) of 6-fluoro-2-[2-(5-nitro-2-furyl)vinyl]-4-chloroquinazoline (IV) is added. The reaction mixture is reacted as in Example I to obtain 6.5 g of crude product, a yellow solid which melts at 241°-242° C. with decomposition. A 5.5 g sample is recrystallized from 40 ml of dimethyl formamide and 74 ml of methanol is added to the warm solution which is then cooled to recrystallize the purified product.

EXAMPLE III

6-fluoro-2-[2-(5-nitro-furyl)vinyl]-4-(o-hydroxyanilino)-quinazoline (VII)

An Erlenmeyer flask equipped with magnetic stirrer and oil bath for heating is charged with 5.0 g (0.046 mole) of o-aminophenol and 100 ml of dimethylformamide. The charge is stirred to dissolve o-aminophenol and 6.0 g (0.02 mole) of 6-fluoro-2-[2-(5-nitro-2-furyl)vinyl]-4-chloroquinazoline (IV) added. The reaction mixture is reacted at 80° to 90° C. for 2 hours to form an organic precipitate; 100 ml of water is added to the warm mixture which is then allowed to cool and placed overnight in a refrigerator to crystallize. The solids are collected, washed with methanol and dried to obtain 7.5 g of brown-tan solid. A solution of the product in 100 ml of dimethylformamide is treated with activated carbon and filtered. A first portion of 75 ml of methanol is added to the warm filtrate then an additional 25 ml portion. Cooling and scratching gives 5.5 g of orange crystals of the purified product.

EXAMPLE IV

6-fluoro-2-[2-(5-nitro-2-furyl)vinyl]-4-anilinoquinazoline (VIII)

A 250 ml flask equipped with stirrer, reflux condenser and thermometer is charged with 4.1 g (0.044 mole) aniline and 100 ml dimethyl formamide. The charge is stirred to dissolve and 6 g (0.02 mole) 6-fluoro-2-[2-(5-nitro-2-furyl)vinyl]-4-chloroquinazoline (IV) is added. The mixture is reacted at 130°-132° C. for 2 hours to form a dark red solution. A 75 ml portion of water is added to the warm solution which is allowed to stand at room temperature overnight, then cooled 1 hour in an ice bath. The crystallized solid is collected, washed with methanol and dried to yield 5.5 g of brown solid. The solid is dissolved in 50 ml warm dimethyl formamide, decolorized with activated carbon, and precipitated by adding 100 ml methanol, with cooling and scratching to induce crystallization. The precipitated solid is collected and washed with methanol to yield the desired product.

EXAMPLE V

7-fluoro-2-[2-(5-nitro-2-furyl)vinyl]-4-(p-hydroxyanilino)-quinazoline (IX)

This compound is prepared in the same manner as 6-fluoro-2-[2-(5-nitro-2-furyl)vinyl]-4-(p-hydroxyanilino)-quinazoline (example I) but starting with 4-fluoroanthranilamine (27 g).

The synthesis of similar (non-nitrofuran) 6-halogenated quinazoline compounds is described in the following references.

Synthesis and histamine H2-antagonist activity of 4-quinazolinone derivatives. Ogawa, Nobuo; Yoshida, Toshihiko; Aratani, Takayuki; Koshinaka, Eiichi; Kato, Hideo; Ito, Yasuo. Chemical & Pharmaceutical Bulletin (1988), 36(8), 2955-67.

Synthesis and biological evaluation of 2-styrylquinazolin-4(3H)-ones, a new class of antimitotic anticancer agents which inhibit tubulin polymerization. Jiang, Jack B.; Hesson, D. P.; Dusak, B. A.; Dexter, D. L.; Kang, G. J.; Hamel, E. Journal of Medicinal Chemistry (1990), 33(6), 1721-8.

Kuo, Sheng-chu; Hour, Mann-jen; Huang, Li-jiau; Lee, Kuo-hsiung. Preparation of 2-phenyl-4-quinazolinones and 2-phenyl-4-alkoxy-quinazolines as anticancer and antiplatelet drugs. U.S. (2002), 23 pp.

6-Alkylamino- and 2,3-Dihydro-3'-methoxy-2-phenyl-4-quinazolinones and Related Compounds: Their Synthesis, Cytotoxicity, and Inhibition of Tubulin Polymerization. Hour, Mann-Jen; Huang, Li-Jiau; Kuo, Sheng-Chu; Xia, Yi; Bastow, Kenneth; Nakanishi, Yuka; Hamel, Ernest; Lee, Kuo-Hsiung. Journal of Medicinal Chemistry (2000), 43(23), 4479-4487.

EXAMPLE VI

6,7-Difluoro-2-Methyl-4-(3H)quinazolinone (X)

4,5-fluoro-Anthranilamide hydrochloride was prepared by adding 10 ml of concentrated hydrochloric acid (37% by weight) to a solution of 10 g of 4,5-difluoroanthranilamide in 100 ml of methanol.

This mixture was cooled in an ice bath to precipitate the hydrochloride which was then collected and dried to obtain a product. A (0.01 mole) portion of the hydrochloride thus obtained was refluxed for 3 hours with 10 ml acetic anhydride and allowed to stand overnight. The mixture was then cooled in an ice bath and the solids collected by filtration on a Buchner funnel. The filter cake was slurried in 10 ml of water, and warmed to enhance dissolution and then 28% aqueous ammonia was added until the mixture was alkaline. After cooling the 6,7-difluoro-2-methyl-4-(3H)quinazolinone precipitated as a solid, was then collected, washed with a small amount of cold water and dried at 70° C. to obtain the desired product.

6,7-Difluoro-2-[2-(5-nitro-2-furyl)vinyl]-4-(p-hydroxyanilino)quinazoline (XI)

This compound was prepared in the same manner as that described in Example I or the synthesis of 6-fluoro-2-[2-(5-nitro-2-furyl)vinyl]-4-(p-hydroxyanilino)quinazoline, by using 6,7-difluoro-2-methyl-4-(3H)quinazolinone (1 g) as a starting material.

The synthesis of 4,5-fluoro-anthranilamide is described in the following references.

Hayes, Thomas K.; Kiely, John S. Tricyclic tetrahydroquinoline derivatives and tricyclic tetrahydroquinoline combinatorial libraries. PCT Int. Appl. (1998), 119 pp. WO 9834111 A1 19980806.

Hayes, Thomas K.; Forood, Behrouz; Kiely, John S. 4-Substituted quinoline derivatives and 4-substituted quinoline combinatorial libraries. PCT Int. Appl. (1998), 124 pp. WO 9834115 A1 19980806.

Gao, Yun. Compositions containing N-amino- and N-hydroxy-quinazolinones and methods for preparing combinatorial libraries thereof. S. (2001), 15 pp. U.S. Pat. No. 6,184,377 B1 20010206.

Desos, Patrice; Lepagnol, Jean M.; Morain, Philippe; Lestage, Piere; Cordi, Alex A. Structure-Activity Relationships in a Series of 2[1H]-Quinolones Bearing Different Acidic Function in the 3-Position: 6,7 Dichloro-2[1H]-oxo-quinoline-3-phosphonic Acid, a New Potent and Selective AMPA/Kainate Antagonist with Neuroprotective Properties. Journal of Medicinal Chemistry (1996), 39(1), 197-206.

Sadhu, Chanchal; Dick, Ken; Treiberg, Jennifer; Sowell, C. Gregory; Kesicki, Edward A.; Oliver, Amy. Preparation of purinylquinazolinones as inhibitors of human phosphatidylinositol 3-kinase delta. U.S. Pat. Appl. Publ. (2002), 86 pp., Cont.-in-part of U.S. Pat. No. 841,341. US 2002161014 A1 20021031.

Sadhu, Chanchal; Dick, Ken; Treiberg, Jennifer; Sowell, C. Gregory; Kesicki, Edward A.; Oliver, Amy. Quinazolinone derivatives as inhibitors of human phosphatidylinositol 3-kinase delta. PCT Int. Appl. (2001), 278 pp WO 0181346 A2 20011101.

EXAMPLE VII

7-(4-methylpiperazino)-6-fluoro-2-Methyl-4-(3H)quinazolinone (XII)

To a solution of 6,7-Difluoro-2-Methyl-4-(3H)quinazolinone (X) (5 mmol) in DMSO (10 ml) was added 4-methylpiperidine (20 mmol). The mixture was heated to 80° C. for 4 h. After cooling water (30 ml) was added and the solid was collected by filtration. The product was further purified by flash chromatography.

7-(4-methylpiperazino)-6-fluoro-2-[2-(5-nitro-2-furyl)vinyl]-4-(3H)quinazolinone (XIII)

This compound was prepared in the same manner as described for 6-fluoro-2-[2-(5-nitro-2-furyl)vinyl]-4-(3H) quinazolinone (III). Thus the desired product was obtained starting with XII (3 mmol).

7-(4-methyl piperazino)-6-fluoro-2-[2-(5-nitro-2-furyl)vinyl]-4-chloroquinazoline (XIV)

This compound was prepared in the same manner as described for 6-fluoro-2-[2-(5-nitro-2-furyl)vinyl]-4-chloroquinazoline (IV). Thus the desired product was obtained starting with XIII (1.5 mmol).

7-(4-methylpiperazino)-6-fluoro-2-[2-(5-nitro-2-furyl)vinyl]-4-(p-hydroxyanilino)-quinazoline (XV)

This compound was prepared in the same manner as described for 6-fluoro-2-[2-(5-nitro-2-furyl)vinyl]-4-(p-hydroxy-anilino)quinazoline (V). Thus the desired product was obtained starting with XIII (1.5 mmol).

EXAMPLE VIII

Methods of Compound Evaluation

Minimal Inhibitory Concentration (MIC) Determination. Bacteria (primary strain panel, TABLE 1). Susceptibility tests were performed following the recommendations from the National Committee for Clinical Standards (NCCLS). The MICs were determined by a broth microdilution technique using a final volume of 100 µl of cation-adjusted Mueller Hinton Broth (MHBCA) and a bacterial inoculum of $10^5$-$10^6$ Colony Forming Units (CFU)/ml. The inocula were verified and precisely determined by applying 10-µl drops of 10-fold dilutions onto Triptic Soy Agar plates. The CFU were counted after an incubation of 24 h at 35° C. Any experiment showing an inoculum that was more or less than $10^5$-$10^6$ CFU/ml was rejected. Control antibiotics and test compounds were prepared at a concentration equivalent to 2-fold the highest desired final concentration. Compounds were then diluted directly in the 96-well microtiter plates by serial 2-fold dilutions using a multichannel pipette. Microtiter plates were incubated during 24 h at 35° C. and growth was recorded by using a microtiterplate reader at 650 nm as well as by visual observation. The MIC was defined as the lowest concentration of compound yielding no visible growth. At least two commercial antibiotics (e.g., imipenem, ciprofloxacin, norfloxacin, nitrofurantoin, rifampicin, chloramphenicol, ampicillin, cefotaxime and vancomycin) were always included as internal microtiter plate controls in each MIC assay. Results from any microtiter plate that showed a discrepancy in such control antibiotic MICs compared to the NCCLS reference data for ATCC strains (a MIC differing by more than 2 doubling dilutions) were rejected. Fastidious bacteria. The medium used for *Listeria monocytogenes, Neisseria meningitidis*, and *Campylobacter jejuni* was MHBCA containing 2% laked horse blood. The medium used for *Haemophilus influenzae* and *Branhamella (Moraxella) catarrhalis* was HTM as recommended by the NCCLS. Cultures of these fastidious bacteria were incubated at 35° C. in a 5% $CO_2$ atmosphere. The MHBCA medium used to grow *M. smegmatis* prior to the MIC assays was supplemented with 0.02% Tween-80 and results from microtiter plates were read after 48 hours of incubation. The medium used for *Bacteroides fragilis* was Wilkins Chalgren broth and growth was allowed under an anaerobic atmosphere at 35° C. for 48 hours.

Finally, compounds were also tested against populations of various clinical strains (antibiotic resistant strain panel, TABLE 1).

TABLE 1

Strain panels used in the evaluation of antimicrobial activity of compounds.

Primary Strain Panel:
   Gram positive.
      *Staphylococcus aureus* ATCC 29213
      *Staphylococcus aureus* MRSA COL
      *Staphylococcus epidermidis* ATCC 12228
      *Staphylococcus saprophyticus* ATCC 15305
      *Enterococcus faecalis* ATCC 29212
      *Enterococcus faecium* ATCC 35667
      *Bacillus cereus* ATCC 11778
      *Bacillus subtilis* ATCC 6633
      *Bacillus atrophaeus* ATCC 9372
      *Listeria monocytogenes*\* ATCC 13932
   Gram negative.
      *Escherichia coli* ATCC 25922
      *Escherichia coli* MC4100
      *Salmonella typhimurium* ATCC 14028
      *Acinetobacter baumannii* ATCC 19606
      *Yersinia enterocolytica* ATCC 23715
      *Haemophilus influenzae*\* ATCC 49247
      *Haemophilus influenzae*\* ATCC 49766
      *Branhamella (Moraxella) catarrhalis*\* ATCC 8176
      *Campylobacter jejuni*\* ATCC 33291
   Anaerobic bacteria.
      *Bacteroides fragilis*\* ATCC 25285
   Acid-Fast bacteria.
      *Mycobacterium smegmatis*\* ATCC 19420
Antibiotic Resistant Strain Panel:
   10  *Staphylococcus aureus* MRSA
    8  *Escherichia coli*
    1  *Enterococcus faecium* VRE (vanA)

Note:
\*= Fastidious bacterial species

Minimal Bactericidal Concentration (MBC). After the microtiter plates were read for the determination of the MIC, a 10-µl sample of each clear well (at least 5 wells without visible growth) was applied onto TSA plates for viable counts determination.

Petri dishes were incubated at 35° C. for exactly 24 h and bacterial colonies were counted. The MBC was the minimal concentration of antibiotic which resulted in 99.9% killing of the original inoculum. For example, if the original inoculum was 1×$10^6$ CFU/ml, the MBC was the concentration showing ≦10 colonies on TSA plate.

Time-kill curves. The bactericidal action of compounds was also evaluated over time (time-kill curve experiments). A bacterial inoculum of 1×$10^5$-1×$10^7$ Colony Forming Units (CFU)/ml was prepared. The inocula were verified and precisely determined by applying 10-µl drops of 10-fold dilutions onto Triptic Soy Agar plates. The CFU were counted after an incubation of 24 h at 35° C. Any experiment showing an inoculum that was more or less than the desired range of CFU/ml was rejected. Time-kill curve experiments were performed in 30 ml of MHB placed in 50-ml shaking flasks over a period of 24 hours. Test compounds and control antibiotics were added at time 0 hour and, at each time point, a sample was removed from flasks and the CFU determined by plate counts as described above. CFU from compound-treated cultures were compared to CFU collected from the control flask without antibiotic. Test compounds and control antibiotics were assayed at the MIC or a multiple of the MIC as determined by a broth microdilution technique as described above.

In vivo efficacy. The antimicrobial activity of compounds was also evaluated in a S. aureus model of systemic infection in the mouse. To produce the systemic infection, CD-1 female mice (20 g) were injected intra-peritoneally with $10^7$ CFU of S. aureus strain Newman suspended in 0.5 ml of endotoxin-free PBS containing 5% mucin (w/v). The compounds were administrated by oral gavage (15 mg/kg) at 1 hour post-infection and kidneys harvested and pooled, for each animal, 5 hours after bacterial inoculation. Tissues were homogenized in PBS and homogenates serially diluted and plated for CFU determination.

Results of Compound Evaluation

Inhibitory activity of Example I (compound V) and Example VII (compound XV). The compounds from Examples I and VII were evaluated against panels of microorganisms as described in TABLE 1 in order to determine their relative potency (MICs and MBCs) and breadth of spectrum. In the results outlined in TABLE 2, many reference microorganisms (American Type Culture Collection, ATCC strains) and many commercially available antibiotics were included in each of the tests used to characterize the activity of Examples I and VII in order to validate measurements and ensure high quality data.

than commercial nitrofurans like nitrofurantoin and nitrofurazone against all strains of TABLE 2.

Compound V was also very active against pathogens often causing urinary tract infections (e.g., S. saprophyticus, TABLE 2, and E. coli, TABLE 3). Against the reference strains, the activity of Compound V was better than commercial nitrofuran agents, like nitrofurantoin, usually used for treatment of urinary tract infections.

The MBCs of Compound V were most of the time equal to or only 2 to 4-fold higher than the MICs showing that this compound was bactericidal and not bacteriostatic.

Compound V also demonstrated a very good activity against three species of the bacterial genus Bacillus (i.e., B. cereus, B. subtilis and B. atrophaeus) with MICs ranging from 0.03 to 0.125 µg/ml (data not shown). Bacillus anthracis, the bacterial pathogen causing anthrax, is also a member of that bacterial genus.

Compounds V and XV showed excellent activity against respiratory tract pathogens causing community-acquired otitis media and pneumonia (TABLE 4). The activity of Compound V was superior to that of the β-lactam drugs (ampicillin, cefotaxime and meropenem) and macrolides

TABLE 2

MICs (and MBCs) in µg/ml for control antibiotics and compounds of Examples I and VII obtained for a variety of Gram positive bacteria from the primary strain panel.

| Antibiotic | S. aureus ATCC 29213 | S. aureus MRSA COL | S. epidermidis ATCC 12228 | S. saprophyticus ATCC 15305 | E. faecalis ATCC 29212 | E. faecium ATCC 35667 |
|---|---|---|---|---|---|---|
| Example I compound V | 0.03-0.06 (0.06) | 0.015 (0.06) | 0.03 (0.03) | 0.015-0.03 (0.03-0.06) | 0.03 (0.03) | 0.06 (0.25) |
| Example VII compound XV | 2 | 0.5 | 1-2 | 2 | 2-8 | 8 |
| Ampicillin | 1-2 | 8 | 64 | 0.12 | 1 | 1 |
| Cefotaxime | 1-2 | 512 | 0.5-1 | 8 | 2-8 | 16 |
| Ceftriaxone | 2 | 512 | 1 | 8 | 8 | 64 |
| Chloramphenicol | 16 | 8 | 8 | 4-8 (16-32) | 8 | 8 |
| Erythromycin | 0.5 | 0.25 | 0.5 | 0.25 | 2-4 | 2 |
| Furazolidone | 4-16 | 8 | 2-4 | 2 | 8-16 | >128 |
| Gentamicin | 0.5-2 | 0.5 | 0.06-0.25 | 0.06 | 4-16 | 4-16 |
| Imipenem | 0.015 | 16 | 0.008-0.015 | 0.03 (0.03-0.06) | 0.5 | 2 |
| Meropenem | 0.06 | 16 | 0.06 | 0.25 | 2-4 | 16 |
| Nitrofurantoin | 16 | 16 | 16 | 8 (16) | 8-16 | 64 |
| Nitrofurazone | 16 | 8-16 | 8 | 8 | 64 | 128 |
| Norfloxacin | 1 | 0.5-1 | 0.5 | 2 (4) | 4 | 16 |
| Oxacillin | 0.12-0.25 | 512 | 0.12 | 1 | 8-16 | 32 |
| Rifampicin | 0.008-0.015 | 0.008-0.015 | 0.004-0.008 | 0.03 | 0.5-1 | 32 |
| Tetracycline | 0.5-1 | 2 | 128 | 1 | 16-32 | 0.5 |
| TMP/SMX (1/19) | 0.06/1.2 | 0.25/4.8-0.5/9.5 | 0.12/2.4-0.25/4.8 | 0.06/1.2 (0.25/4.8) | 0.015/0.3 | 0.12/2.4 |
| Vancomycin | 0.5-2 | 1-2 | 1-2 | 1 (1) | 2 | 0.5 |

Compound V and Compound XV showed exquisite activities against Gram positive bacteria generally causing severe opportunistic and/or nosocomial infections (TABLE 2). These included Methicillin-Resistant and Methicillin-Sensitive S. aureus strains [MRSA and MSSA, respectively], S. epidermitidis, E. faecalis and E. faecium. The activity of Example I was better than that of imipenem, norfloxacin, vancomycin or several other commercial antibiotics against MRSA, E. faecalis and E. faecium. Compound XV was better (erythromycin, clarithromycin) against H. influenzae ATCC 49247 and B. catarrhalis. Compounds V and XV were also very active against Mycobacterium smegmatis and their activity was superior to that of the commercial nitrofurans, norfloxacin and rifampicin. Mycobacterium tuberculosis, the bacterial pathogen causing tuberculosis, is a member of that bacterial genus. Compound V was very active against L. monocytogenes and C. jejuni causing enteric infections and against B. fragilis, an anaerobe often causing difficult-to-treat abscesses and infections in diabetic patients.

TABLE 3

MICs (and MBCs) in μg/ml for control antibiotics and compound of Example I
obtained for a variety of Gram negative bacteria from the primary strain panel.

| Compounds | E. coli ATCC 25922 | S. typhimurium ATCC 14028 | A. baumannii ATCC 19606 | Y. enterocolytica ATCC 23715 |
|---|---|---|---|---|
| Example I compound V | 0.5 (0.5) | 1 | 1-2 | 0.25 |
| Ampicillin | 4-8 | — | — | — |
| Meropenem | 0.015-0.06 | — | 2 | >0.5 |
| Chloramphenicol | 4 (16) | — | — | — |
| Cefotaxime | 0.06-0.12 | >2 | 16 | >2 |
| Imipenem | 0.12 | — | 16 | 0.5 |
| Ceftriaxone | 0.03-0.06 | — | — | — |
| Oxacillin | 512->512 | — | — | — |
| Erythromycin | 64 | — | — | — |
| Rifampicin | 8 | — | 4 | 8 |
| Norfloxacin | 0.03 (0.06) | — | — | — |
| Tetracycline | 1-2 | — | 16 | >32 |
| Gentamicin | 0.5-2 | — | 32 | 2 |
| Nitrofurantoin | 8 (8) | 32 | 128 | 64 |
| Nitrofurazone | 8-16 | 8 | 32 | 64 |
| Furazolidone | 1-2 | 2 | 32 | >16 |
| TMP/SMX (1/19) | 0.25/4.75-0.5/9.5 | — | 8/152 | 0.125/2.4 |

TABLE 4

MICs (and MBCs) in μg/ml of control antibiotics and compounds of Examples I and VII
obtained for Gram negative, Gram positive and acid-fast fastidious bacterial species.

| Compounds | H. influenzae ATCC 49247 | H. influenzae ATCC 49766 | B. catarrhalis ATCC 8176 | M. smegmatis ATCC 19420 |
|---|---|---|---|---|
| Example I compound V | 0.03 (0.06) | 0.06 (0.06) | 0.008 (0.03) | 0.06 |
| Example VII compound XV | 2 | 2 | 0.5 | 0.25 |
| Ampicillin | 2-4 (4) | ≦0.12 (≦0.12) | ≦0.03 (≦0.03) | — |
| Cefotaxime | 0.12 (0.12) | 0.008 (0.008) | 0.03 (0.06) | — |
| Ciprofloxacin | 0.008-.015 (0.015) | 0.008 (0.015) | 0.03 (0.06) | — |
| Clarithromycin | 16 | 128 (>128) | 0.5 (1) | — |
| Erythromycin | 2 (2) | 8 (16) | 0.06 (0.12) | — |
| Meropenem | 0.06 (0.06) | 0.03 (0.06) | 0.002 (0.008) | — |
| Nitrofurantoin | — | — | — | 64 |
| Nitrofurazone | — | — | — | 64 |
| Norfloxacin | — | — | — | 2 |
| Rifampicin | — | — | — | 8 |

| Compounds | L. monocytogenes ATCC 13932 | C. jejuni ATCC 33291 | B. fragilis ATCC 25285 |
|---|---|---|---|
| Example I compound V | 0.03-0.25 | 0.016 | 0.016 |
| Example VII compound XV | 0.5 | — | 0.5 |
| Chloramphenicol | 0.001 | 4 | 4 |
| Rifampicin | 0.06 | — | — |
| Norfloxacin | 0.008 | — | — |
| Tetracycline | — | 0.5 | 0.25 |
| Imipenem | — | 0.125 | 0.125-0.5 |

The activity of Compounds V and XV was not influenced by the resistance mechanisms residing in multi-resistant *E. faecium* (e.g., strain VanA, TABLE 5). Similarly, the activity of Compounds V and XV was not influenced by the resistance mechanisms residing in multi-resistant MRSA strains (TABLE 6). This data was outstanding considering that at least 80% of the strains that were tested were resistant to many antibiotics of the conventional arsenal (e.g., oxacillin, erythromycin, norfloxacin).

The activity of Compound V was also not influenced by the resistance mechanisms residing in multi-resistant *E. coli* (e.g., strains Ec022c, Ec027c, Ec117c, Ec118c, and Ec119c, TABLE 7) or by the pathotype, i.e., the virulence characteristics of the strains (e.g., Entero-Hemorrhagic *E. coli* O157: H7 or Extra-Intestinal *E. coli* EIEC, TABLE 7).

The activity of Compounds V and XV against multi-resistant microorganisms, i.e., that are resistant to at least two structural classes of drugs, indicates that the chemical nature of the nitrofurans of the present invention was not previously encountered by such strains or did not elicit the development of resistance among these strains as opposed to all the other antibiotic classes that were tested (TABLES 5, 6, and 7).

TABLE 5

MICs in μg/ml of control antibiotics and compounds
of Examples I and VII obtained for antibiotic
multi-resistant *Enterococcus faecium* (VanA).

| Compounds | E. faecalis ATCC 29212 | E. faecium ATCC 35667 | E. faecium VanA |
|---|---|---|---|
| Example I compound V | 0.03 | 0.06 | 0.03 |
| Example VII compound XV | 2-8 | 8 | 0.5 |

TABLE 5-continued

MICs in μg/ml of control antibiotics and compounds of Examples I and VII obtained for antibiotic multi-resistant *Enterococcus faecium* (VanA).

| Compounds | E. faecalis ATCC 29212 | E. faecium ATCC 35667 | E. faecium VanA |
|---|---|---|---|
| Vancomycin | 2 | 0.5 | >128 |
| Cefotaxime | 2-8 | 16 | >128 |
| Clarithromycin | 16 | — | >128 |
| Tetracycline | 16-32 | 0.5 | 128 |
| Rifampicin | 0.5-1 | 32 | >128 |
| Furazolidone | 8-16 | >64 | 64 |
| Nitrofurazone | 64 | >64 | 64 |

TABLE 6

MICs in μg/ml for control antibiotics and compounds of Examples I and VII obtained for a variety of antibiotic multi-resistant MRSA strains.

| MRSA strains (n = 10) | Example I compound V | Example VII compound XV | Oxacillin | Erythromycin | Norfloxacin | Gentamicin | Nitrofurantoin |
|---|---|---|---|---|---|---|---|
| MRSA COL | 0.015 | 0.5 | >128 | 0.25 | 1 | 0.5 | 8-16 |
| Sa211c | ≦0.06 | 2 | 16-32 | >32 | >32 | 1 | 16-32 |
| Sa212c | 0.125 | 4 | 16 | >32 | >32 | 0.25 | 32 |
| Sa220c | ≦0.06 | 0.25 | 8-16 | 0.5 | >32 | 0.5 | 16 |
| Sa224c | ≦0.06 | 1 | 32-64 | >32 | >32 | 0.25 | 16 |
| Sa228c | ≦0.06 | 2 | 128 | >32 | >32 | 32 | 16-32 |
| Sa234c | ≦0.06 | 2 | 32->128 | >32 | >32 | 1 | 16-32 |
| Sa248c | ≦0.06 | 0.5 | 512 | >128 | 32 | >128 | 16 |
| Sa249c | ≦0.06 | 0.5 | 512 | >128 | 32 | >128 | 16 |
| Sa253c | ≦0.06 | 2 | 1024 | >128 | >128 | >128 | 16 |

TABLE 7

MICS in μg/ml for control antibiotics and compound of Example I obtained for a variety of antibiotic resistant *E. coli* strains and/or of different pathotypes.

| E. coli strains (n = 10) | Pathotype | Example I compound V | Ampicillin | Ciprofloxacin | Nitrofurantoin | TMP-SMX (1/19) | Tetracycline |
|---|---|---|---|---|---|---|---|
| ATCC 25922 | Reference | 0.5 | 4 | 0.03 | 8-16 | 0.25/4.75-0.5/9.5 | 2 |
| MC4100 | Reference | 1 | 4 | — | 8-16 | — | — |
| ATCC 35150 | O157:H7 | 1 | 2 | ≦0.25 | 2 | 0.03/0.6 | 2 |
| d4-OLR-pen10 | O157:H7 | 1 | 2-4 | ≦0.25 | 16 | 0.125/2.4 | >32 |
| d25-ALR-pen14 | O157:H7 | 1 | 2-4 | ≦0.25 | 16 | 0.125/2.4 | >32 |
| Ec022c | EIEC | 1 | >64 | 0.015-0.03 | 16 | >2/38 | 2 |
| Ec027c | EIEC | 1 | >64 | 0.015 | 16 | 0.03/0.6 | >32 |
| Ec117c | EIEC | 1 | 16 | >128 | 8-16 | >2/38 | >32 |
| Ec118c | EIEC | 1 | >64 | 64 | 16 | >2/38 | 4 |
| Ec119c | EIEC | 2 | >64 | 32 | 16 | >2/38 | >32 |

Figure 1:
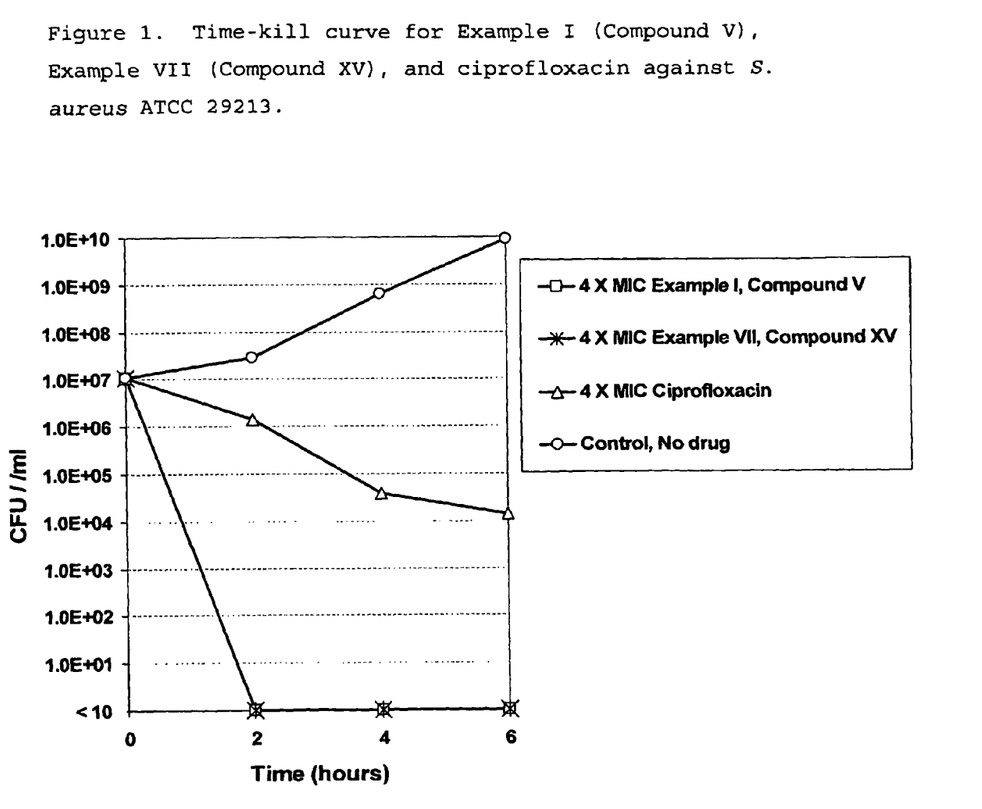
FIG. 1. Time-kill curve for compound 6-fluoro-2-[2-(5-nitro-2-furyl)vinyl]-4-(p-hydroxyanilino)quinazoline (Compound V, Example I), compound 7-(4-methylpiperazino)-6-fluoro-2-[2-(5-nitro-2-furyl)vinyl]-4-(p-hydroxyanilino) quinazoline (Compound XV, Example VII) and ciprofloxacin against *S. aureus* ATCC 29213.
Figure 2:
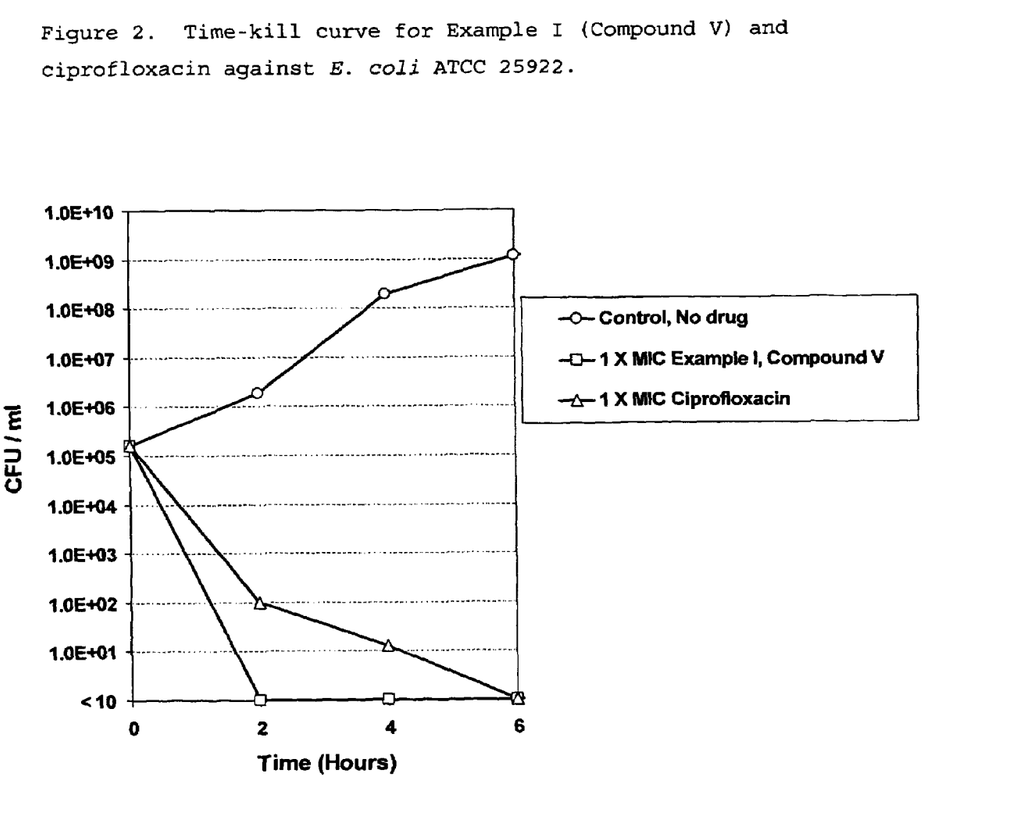
FIG. 2. Time-kill curve for compound 6-fluoro-2-[2-(5-nitro-2-furyl)vinyl]-4-(p-hydroxyanilino)quinazoline (Example I, Compound V) and ciprofloxacin against *E. coli* ATCC 25922.

Bactericidal activity of Compounds V and XV. Compound V of Example I and Compound XV of Example VII were evaluated in time-kill studies against *S. aureus* and/or *E. coli* (FIGS. 1 and 2, respectively). Results showed that Compounds V and VII were strongly bactericidal within 2 hours against the tested strains. Compound V was superior to ciprofloxacin at their respective MIC or a multiple of the MIC against both species. Compound V was similarly bactericidal against strain *S. aureus* MRSA COL showing that it is also able to kill bacteria resistant to commonly used antibiotics (data not shown).

Figure 3:
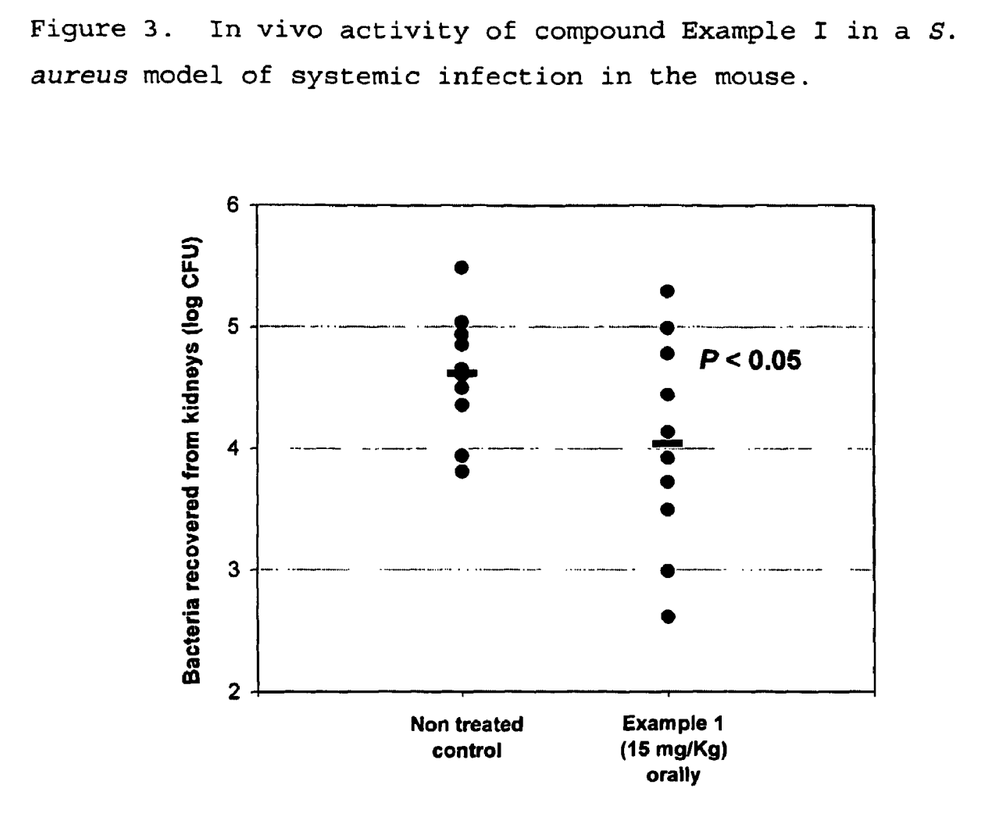
FIG. 3. In vivo activity of compound 6-fluoro-2-[2-(5-nitro-2-furyl)vinyl]-4-(p-hydroxyanilino)quinazoline (Example I, Compound V) in a *S. aureus* model of systemic infection in the mouse.

In vivo activity of Compound V. Compound V was active in vivo. FIG. 3 reports the results of a *S. aureus* peritonitis model of infection in the mouse. Results clearly showed that Compound V reduced significantly the presence of viable bacteria in the kidneys. This important result demonstrated oral bioavailability of Compound V and its relatively low toxicity in vivo.

Solubility of Compounds V and XV. The extent of solubility of compounds was evaluated in water. Compound V was soluble in water (no visible particles) at a concentration of 0.25 mg/ml, whereas Compound XV was 4 times more soluble (i.e., 1 mg/ml).

All patents, patent applications and publications mentioned herein, both supra and infra, are hereby incorporated by reference.

While the invention has been described with reference to certain specific embodiments and will be described in the following Examples, it is understood that it is not to be so limited since alterations and changes may be made therein which are within the full and intended scope of the appended claims.

The invention claimed is:

1. A compound of the formula (1.0)

wherein

X is absent or trans or cis CHCH;

$R_1$ is phenyl or hydroxyphenyl;

$R_2$ is hydrogen, phenyl or hydroxyphenyl; and $R_3$ and $R_4$ are, independently of each other, H, halogen, or (1.2)

wherein:

P and R are each independently selected from $CH_2$, $CH_2CH_2$ and $CH_2CHT$ where T is alkyl, and Q is O, S, NH or $NCH_3$, with the proviso that at least one of $R_3$ and $R_4$ is halogen; or a pharmaceutically acceptable salt thereof.

2. A compound according to claim 1 of the formula 6-fluoro-2-[2-(5-nitro-2-furyl) vinyl]-4-(p-hydroxyanilino)-quinazoline, wherein vinyl is cis or trans.

3. A compound according to claim 1 of the formula 7-(4-methylpiperazino)-6-fluoro-2-[2-(5-nitro-2-furyl) vinyl]-4-(p-hydroxyanilino)-quinazoline, wherein vinyl is cis or trans.

4. A process for the preparation of the compound according to claim 1 comprising:

a) reacting a compound of formula (1.3)

(1.3)

with hydrochloric acid, acetic anhydride and aqueous ammonia, to form a compound of formula (1.4)

(1.4)

b) reacting the compound of formula 1.4 with 5-nitro-2-furancarboxaldehyde, to form a compound of formula (1.5)

(1.5)

c) reacting the compound of formula 1.5 with phosphorus pentachloride and phosphorus oxychloride to form a compound of formula (1.6)

(1.6)

and d) reacting the compound of formula 1.6 with a compound of the formula (1.7)

(1.7)

wherein $X_1$ is H, and $R_1$, $R_2$, $R_3$, and $R_4$ are as defined in claim 1, with the proviso that at least one of $R_3$ and $R_4$ is halogen.

5. The compound according to claim 1 of the formula 7-fluoro-2-[2-(5-nitro-2-furyl) vinyl]-4-(p-hydroxyanilino)-quinazoline, wherein vinyl is cis or trans.

6. The process according to claim 4, wherein the compound of formula (1.6) is 6-fluoro-2-[2-(5-nitro-2-furyl) vinyl]-4-chloroquinazoline, wherein vinyl is cis or trans.

7. The process according to claim 4, wherein the compound of formula (1.6) is 7-(4-methylpiperazino)-6-fluoro-2-[2-(5-nitro-2-furyl) vinyl]-4-chloroquinazoline, wherein vinyl is cis or trans.

8. The process according to claim 4, wherein the compound of formula (1.5) is 6-fluoro-2-[2-(5-nitro-2-furyl) vinyl]-4-(3H)quinazolinone, wherein vinyl is cis or trans.

9. The process according to claim 4, wherein the compound of formula (1.5) is 7-(4-methylpiperazino)-6-fluoro-2-[2-(5-nitro-2-furyl) vinyl]-4-(3H) quinazolinone, wherein vinyl is cis or trans.

* * * * *